(12) United States Patent
Davila

(10) Patent No.: US 11,376,041 B2
(45) Date of Patent: Jul. 5, 2022

(54) SYSTEM AND METHOD FOR PARAURETHRAL SUPPORT RESTORATION TO TREAT STRESS INCONTINENCE

(71) Applicant: Simplified Surgical Solutions, LLC, Pompano Beach, FL (US)

(72) Inventor: Guillermo Davila, Fort Lauderdale, FL (US)

(73) Assignee: SIMPLIFIED SURGICAL SOLUTIONS, LLC, Pampano Beach, FL (US)

(*) Notice: Subject to any disclaimer, the term of this patent is extended or adjusted under 35 U.S.C. 154(b) by 0 days.

(21) Appl. No.: 17/435,932

(22) PCT Filed: Jun. 5, 2020

(86) PCT No.: PCT/US2020/036266
§ 371 (c)(1),
(2) Date: Sep. 2, 2021

(87) PCT Pub. No.: WO2020/247717
PCT Pub. Date: Dec. 10, 2020

(65) Prior Publication Data
US 2022/0125481 A1    Apr. 28, 2022

Related U.S. Application Data

(60) Provisional application No. 62/857,918, filed on Jun. 6, 2019.

(51) Int. Cl.
*A61B 17/34* (2006.01)
*A61B 17/04* (2006.01)
(Continued)

(52) U.S. Cl.
CPC ...... *A61B 17/3468* (2013.01); *A61B 17/0482* (2013.01); *A61B 17/0483* (2013.01);
(Continued)

(58) Field of Classification Search
CPC . A61B 17/3468; A61B 90/08; A61B 17/0482; A61B 17/0483; A61B 2090/0811; A61B 2017/00805; A61B 2017/06176
See application file for complete search history.

(56) References Cited

U.S. PATENT DOCUMENTS 6,068,591 A    5/2000  Bruckner et al.
6,752,814 B2   6/2004  Gellman et al.
(Continued)

OTHER PUBLICATIONS

International Application No. PCT/US2020/036266—Patent Cooperation Treaty PCT International Search Report—Completed Aug. 3, 2020 (dated Aug. 18, 2020).
(Continued)

*Primary Examiner* — George J Ulsh
(74) *Attorney, Agent, or Firm* — Lott & Fischer, PL

(57) ABSTRACT

Disclosed are a system and method to implement a novel treatment to restore bilateral longitudinal parallel paraurethral support, the system comprising a trocar, and introducer, and one or more barbed suture-type devices, the components used cooperatively to implant the one or more barbed suture-type devices in the patient to provide sufficient paraurethral support to restore continence in the patient.

13 Claims, 6 Drawing Sheets

(51) Int. Cl.
*A61B 90/00* (2016.01)
*A61B 17/00* (2006.01)
*A61B 17/06* (2006.01)

(52) U.S. Cl.
CPC .... *A61B 90/08* (2016.02); *A61B 2017/00805* (2013.01); *A61B 2017/06176* (2013.01); *A61B 2090/0811* (2016.02)

(56) References Cited

U.S. PATENT DOCUMENTS

| | | |
|---|---|---|
| 8,467,875 B2 | 6/2013 | Bennett et al. |
| 8,944,990 B2 | 2/2015 | Hamel et al. |
| 2002/0055748 A1* | 5/2002 | Gellman ............ A61B 17/0218 606/139 |
| 2006/0173468 A1 | 8/2006 | Simmon et al. |
| 2009/0171143 A1* | 7/2009 | Chu ................. A61B 17/06109 600/37 |
| 2010/0010631 A1* | 1/2010 | Otte ..................... A61F 2/0004 606/155 |
| 2013/0023724 A1* | 1/2013 | Allen ................. A61B 17/0401 600/30 |

OTHER PUBLICATIONS

International Application No. PCT/US2020/036266—Patent Cooperation Treaty PCT Written Opinion of the International Searching Authority—Completed Aug. 3, 2020 (dated Aug. 18, 2020).

* cited by examiner

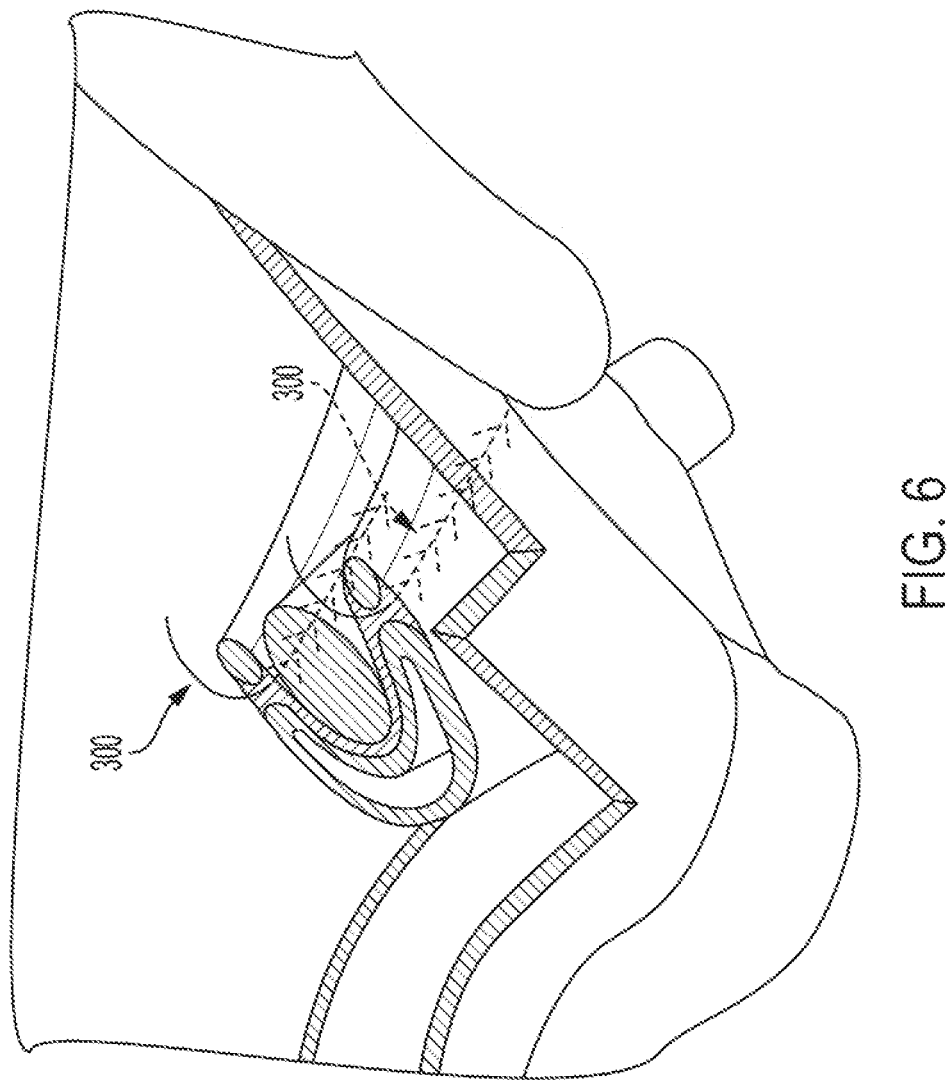

SYSTEM AND METHOD FOR PARAURETHRAL SUPPORT RESTORATION TO TREAT STRESS INCONTINENCE

This application is a national phase of PCT Application No. PCT/US2020/036266 filed Jun. 5, 2020, which in turn claims the priority to U.S. Provisional Patent Application No. 62/857,918 filed Jun. 6, 2019.

TECHNICAL FIELD

The present invention is directed to treatments and devices for incontinence. More specifically, disclosed are devices and methods for treatment of female stress incontinence through restoration of paraurethral support.

BACKGROUND ART

In normal women, the urethra is supported by an interaction of the pelvic floor musculature, endopelvic fascia and bilateral attachments to the backside of the pubic symphysis and anterior pelvis. Until recently, the focus for treatment of incontinence caused by impaired urethral support has been on providing mid-urethral support by re-creating pubo-urethral ligaments which provide support at the level of the pelvic floor/levator musculature.

Prior to that, the most commonly used anti-incontinence procedure attached the proximal urethra and bladder neck to the ipsilateral Cooper's ligament with multiple sutures—and was termed a retropubic urethropexy or Burch colosuspension.

Specifically, current methods focus on mid-urethral sling procedures which kink the mid-urethra when under strain. Success rates in restoring continence are at most 90%, suggesting that there is more to the mechanism of urethral support responsible for continence.

Recently, greater degrees of understating of urethral support have focused on maintenance of urethral length providing support to the mechanism of action of retropubic urethropexy. In nulliparous women, longitudinal bilateral attachments to the posterior aspect of the pubic symphysis are identifiable as paraurethral indentations extending from the distal urethra to the bladder neck at the superior edge of the pubic bone.

This paraurethral support maintains urethral length and kinking at the bladder neck during strain maneuvers such as coughing. With the vaginal delivery process and repetitive life-long increases in intra-abdominal pressure, the paraurethral support mechanism becomes attenuated resulting in impaired urethral support, excess urethral mobility, and the development of stress urinary incontinence.

SUMMARY OF INVENTION

The object of the present invention is to restore bilateral longitudinal parallel paraurethral support in order to restore continence in women with stress incontinence due to loss of paraurethral support.

The present invention provides a system, and a method of use to implement a novel treatment to restore bilateral longitudinal parallel paraurethral support, the system comprising at least one rigid trocar, at least one flexible introducer, and one or more flexible barbed suture-type devices. These components are used cooperatively to implant the one or more barbed suture-type devices in the patient bilaterally parallel to the urethra and attached to suprapubic support structures including fascia and ligaments. Once properly implanted the barbed suture-type devices provide sufficient paraurethral support to restore continence in the patient.

BRIEF DESCRIPTION OF DRAWINGS

FIG. 6 illustrates a sagittal view of the top of the urethra with barbed suture-type device components in place bilaterally in accordance with one embodiment of the present invention.

DESCRIPTION OF EMBODIMENTS

Figure 1:
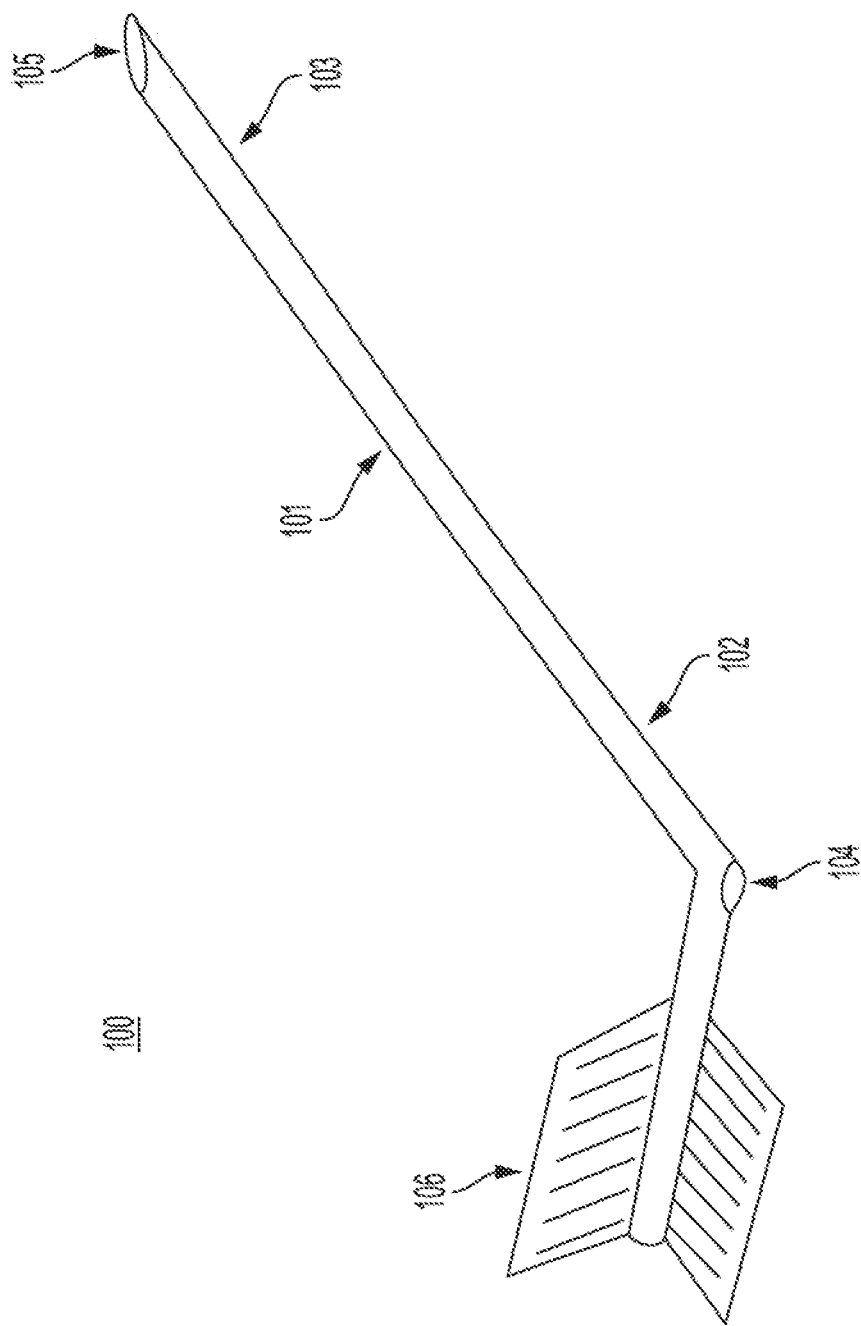
FIG. 1 illustrates a trocar component in accordance with one embodiment the present invention.
Figure 2:
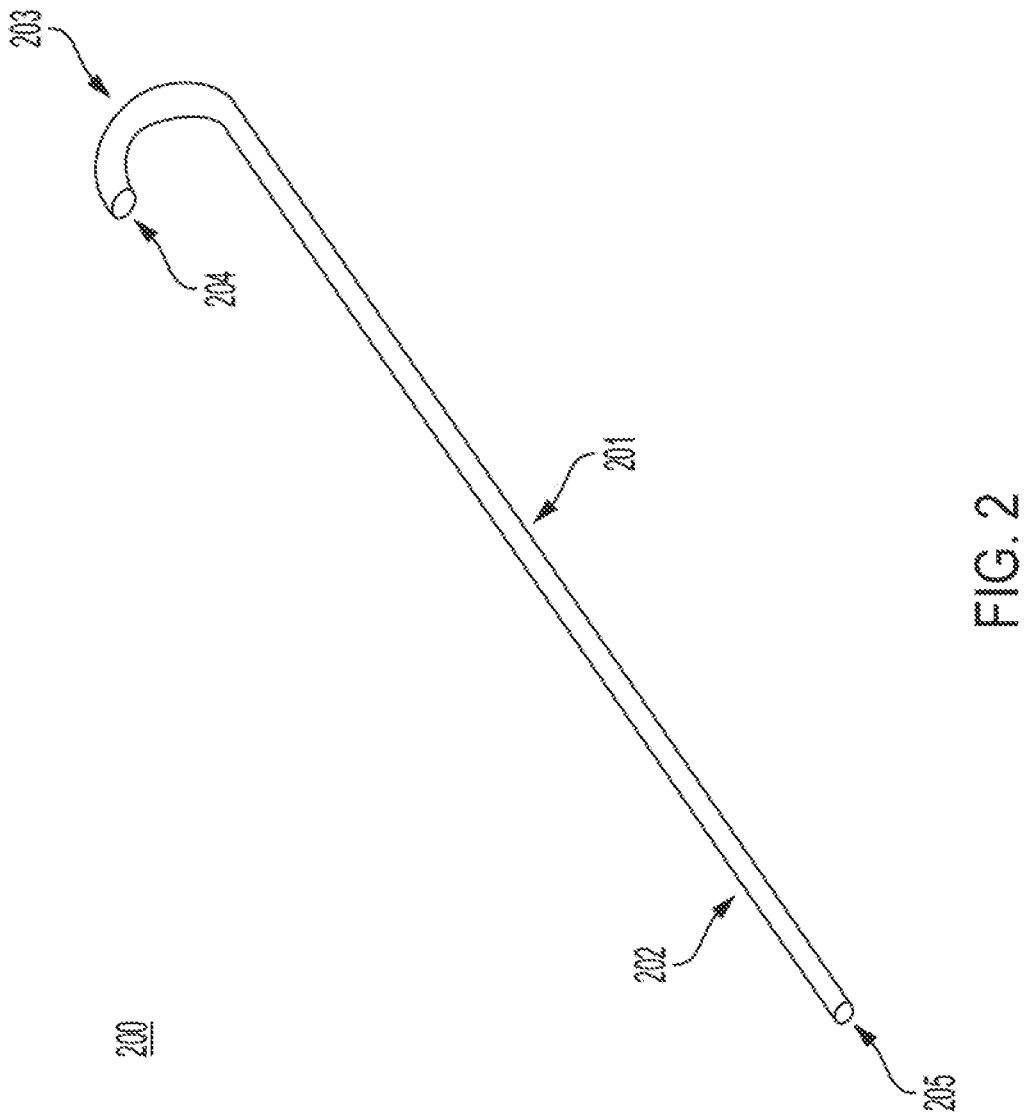
FIG. 2 illustrates an introducer component in accordance with one embodiment the present invention.
Figure 3:
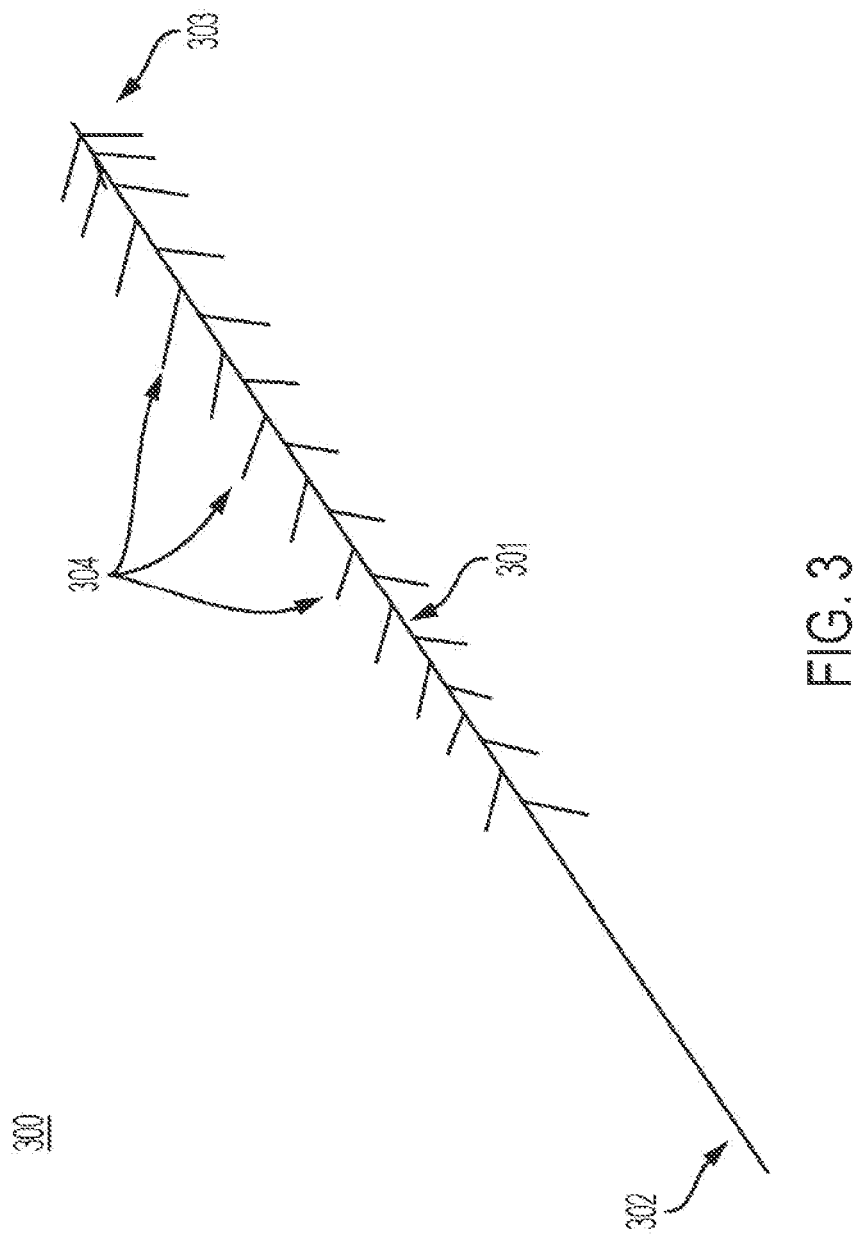
FIG. 3 illustrates a barbed suture-type device component in accordance with one embodiment the present invention.

System Features and Construction:

Referring to FIGS. 1-3 the component devices of the system of the present invention comprise at least one trocar (100), at least one introducer (200); and at least one barbed suture-type device (300). Because in almost all situations the barbed suture-type device (300) will be implanted bilaterally to the urethra, at least two barbed suture-type devices (300) will be required in most cases. However, it is not beyond the scope of the present invention to utilize a single barbed suture-type device (300) applied unilaterally. Moreover, where additional support is required, multiple barbed suture-type devices (300) may be implanted on either, or both, sides of the urethra. Therefore, it is also possible for the system to comprise more than two barbed suture-type devices (300).

The purpose of the trocar (100) and introducer (200) is to aid in the implanting of the barbed suture-type device (300) along the urethral length to restore physiologic paraurethral support.

Referring to FIG. 1 the trocar (100) comprises a lumen portion (101) having proximal and distal ends (102,103) as well as proximal and distal openings (104,105). The lumen portion (101) may be straight or curved to accommodate anatomical variations. A handle (106) attached near the proximal end (102) is adapted to permit manipulation of the trocar (100) during use. The tip of the distal end (103) of the lumen portion (101) may be sharpened to ease introduction. The bore of the lumen portion (100) is large enough to accommodate the outside diameter of introducer (200) (e.g. 14G) and is adapted to be inserted on either side of the urethral meatus. The length of the lumen portion (101) is sufficient to advance from the meatus to the top of the pubic bone. Trocar (101) is substantially rigid and may be made up from a number of different surgically suited rigid materials including metals, polycarbonates, and the like.

Referring to FIG. 2, introducer (200) comprises a substantially elongated hollow cylindrical body (201) having proximal and distal ends (202,203), as well as distal and proximal openings (204,205) disposed therein. The body is of sufficient length to traverse the entire length of the lumen portion (101) of the trocar (100). The outer diameter of the body (201) must be small enough to fit within the lumen portion (101). The inner diameter of the body (201) must be large enough to permit at least one barbed suture-type device (300) fit within it. The distal end (203) of the introducer (200) may optionally be curved to facilitate placement of the barbed suture-type device (300) during the procedure and to prevent bladder wall perforation. The introducer (200) may optionally also include indicia (not shown) on the proximal end (202) to indicate the orientation of the curved distal end (203). The construction of the introducer (200) is substantially flexible but resilient. The optional curved tip can be straightened for introduction into, and advancement through the lumen portion (101) of the trocar (100) but will immediately spring back to its curved shape when it emerges from the distal opening (105) of the trocar (100). Introducer (200) may be made up from aa number of different surgically suited flexible materials including nitinol, polycarbonates, metals, and the like.

Referring to FIG. 3, barbed suture-type device (300) comprises a central elongated suture-type thread (301), having a proximal end (302) and a distal end (303), and a plurality of short barbs (304) extending from the thread (301). The barbs (304) may extend in the direction of the proximal end (302) or in the direction of the distal end (303). Barbs (304) extending in the direction of the proximal end (302) will provide, once implanted in the paraurethral tissue, resistance to movement in the proximal direction. Barbs (304) extending in the direction of the distal end (303) will provide, once implanted in the paraurethral tissue, resistance to movement in the distal direction. The amount of resistance to movement, and thus the level of support, provided by the barbed suture-type device, can be adjusted by varying the flexibility of the barb material, or by changing the density of the barbs (304) within the thread. Moreover, barb (304) flexibility, density, direction, and placement may vary along the length of the thread (301) to provide various levels of resistance along the length of the device.

The barbed suture-type device (300) comprises a semi-rigid but bendable material, such as polypropylene, and the like. The barbed suture-type device (300) is of a size adapted to be loaded into the introducer (200) and advanced through the trocar (200) (e.g. size A #1 to #3 sutures) to be positioned along the length of the urethra from the top of the pubic bone, with attachment of the abdominal wall fascia, to the external urethral meatus. Proximal end (302) of the barbed suture-type device (300) may optionally comprise a needle tip, soft tissue anchor, or dart (not shown) adapted to penetrate through the ipsilateral Cooper's ligament.

Method of Use:

The procedure of the present invention may be performed in the doctor's office or in the surgical suite. A diagnosis of stress urinary incontinence is made. Urethral mobility is assessed.

The patient is placed in stirrups and a Foley catheter is placed in the bladder. A rigid catheter guide can optionally be placed into the foley catheter lumen in order to clearly identify the location of the urethra during the surgical procedure.

Local anesthetic (e.g. 1% lidocaine) is injected along the length of the urethra to the bladder neck and suprapubic lower abdominal wall bilaterally.

Figure 4:
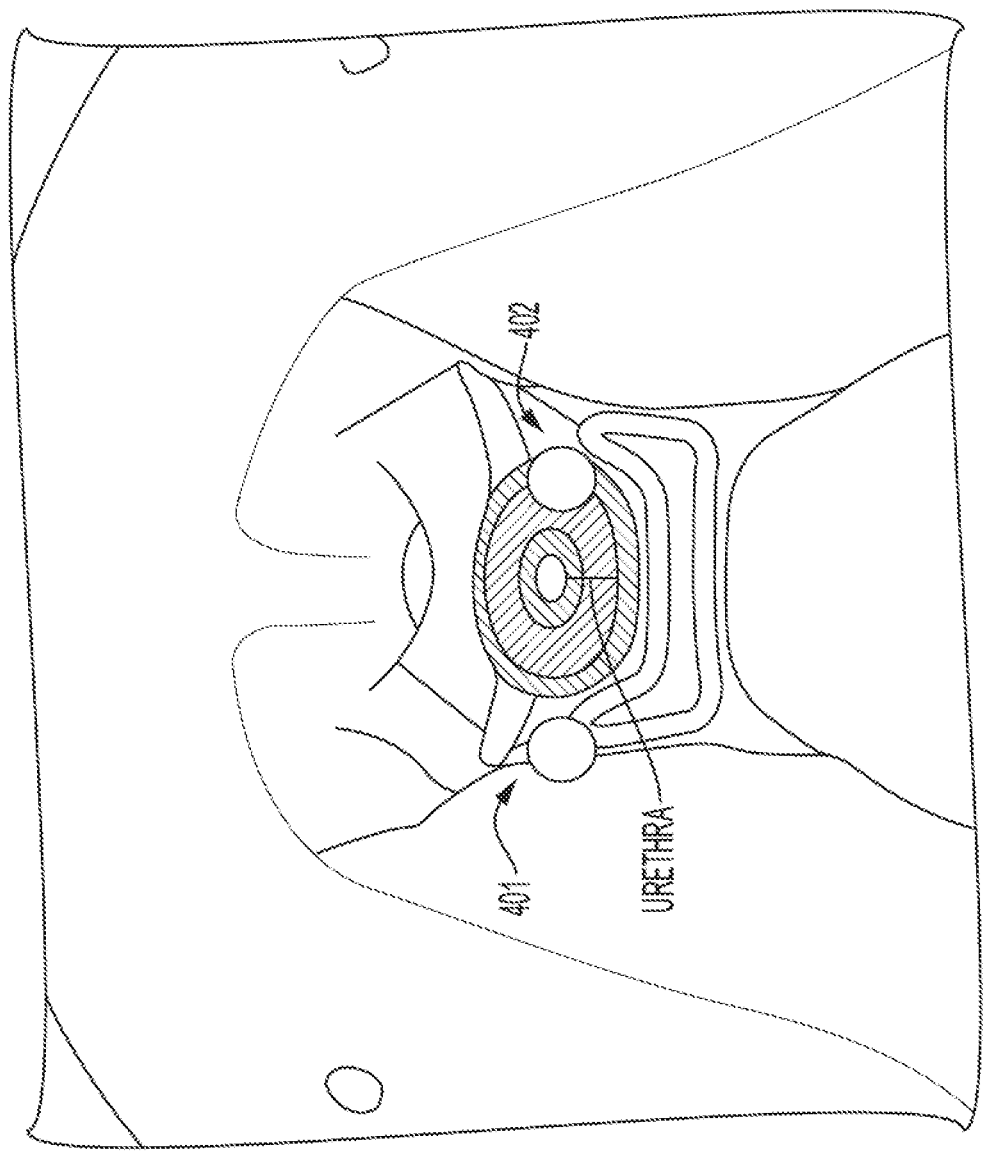
FIG. 4 illustrates a cross sectional view of the female urethra showing the general target placement for the barbed suture components in accordance with one embodiment of the present invention

The trocar (100) is inserted a few millimeters lateral the urethral meatus (see FIG. 4, locations 401 and 402) and advanced along the urethra to the top of the pubic bone and until it indents the abdominal fascia and is palpable through the abdominal wall skin. The trocar can be directed towards the medial portion of the ipsilateral Cooper's ligament. This is performed bilaterally.

Cystoscopy is performed with a 70 scope to confirm bladder wall integrity. If the bladder was perforated, the trocar (100) is repositioned, and cystoscopy repeated.

The barbed suture-type device (300) is loaded onto the introducer (200) by inserting the distal end (303) of the barbed suture-type device (300) into the proximal opening (204) of the introducer (200). The barbed suture-type device (300) is pushed through the introducer (200) until the distal end (303) of the barbed suture-type device (300) emerges out of the distal opening (205) of the introducer (200).

The distal end (203) of the suture-loaded introducer (200) is then inserted into the proximal opening (104) of the trocar (100) and advanced along the lumen portion (101) of the trocar (100) until the distal end (203) of the introducer (200) is palpable along the anterior abdominal wall.

The introducer (200) is advanced until it is positioned at the desired position, possibly through Cooper's ligament and even full thickness through the abdominal wall skin and held in place, The trocar (100) is then removed.

The introducer (200) and trocar (100) are then slowly removed being careful to leave the barbed suture-type device (300) in place along the insertion tract.

Any excess suture material is cut at the level of the external urethral meatus and abdominal wall skin if that is perforated. If the skin does not seal itself, tissue glue can be applied.

Additional Observations:

The barb (304) direction on the barbed suture-type device (300) can vary depending on support needs. For example, facing proximally at one end and distally at the other.

More than one barbed suture-type device (300) per side of the urethra may be required to enhance support.

The distal and/or proximal end (302,302) of barbed suture-type device (300) may require a higher density of polypropylene and type of barbs in order to enhance support.

The barbed suture-type device (300) may be advanced over top of pubic bone or into Cooper's ligament (using a curved tip introducer (200)) or simply towards abdominal wall (using a straight tip introducer (not shown)). A soft tissue anchor may be optionally used at the distal end of barbed suture-type device (300) to enhance support.

Figure 5B:
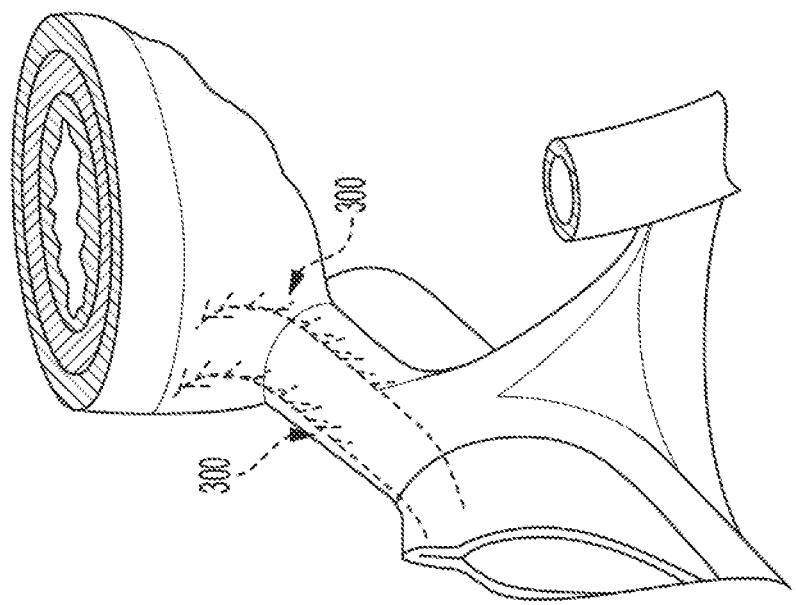
FIGS. 5A and 5B illustrate, respectively, frontal and sagittal views of the bladder with barbed suture components in place bilaterally in accordance with one embodiment of the present invention.
Figure 5A:
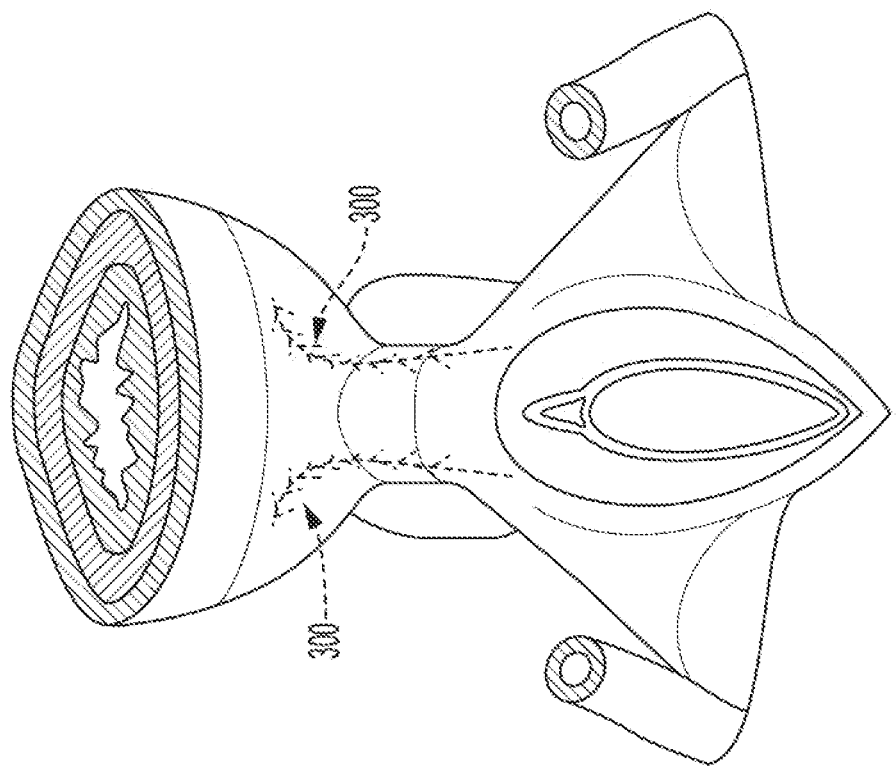

Shown in FIGS. 5A and 5B respectively, are frontal and sagittal views of the bladder with barbed suture-type devices (300) in place bilaterally after placement using the above-described method. FIG. 6 illustrates a sagittal view of the top of the urethra with barbed suture-type devices (300) in place bilaterally in accordance with the present invention.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the described embodiments, features, benefits, methods, and examples, but by all embodiments and methods within the scope and spirit of the invention as described and claimed.

I claim:

1. A system for restoration of paraurethral support in a female patient comprising:
   a substantially rigid trocar comprising a lumen portion having an inside diameter, a proximal end with a proximal opening into said lumen, a terminal end with a terminal opening into said lumen, a handle extending laterally form the proximal end of the lumen portion, the trocar adapted for insertion of the distal end of the lumen portion laterally to the female patient's urethra and advancement of the distal end of the lumen portion to the top of the female patient's pubic bone;

an flexible and resilient introducer comprising a substantially elongated hollow cylindrical body having a proximal end with a proximal opening, a distal end with a distal opening, an inside diameter, an outside diameter, and a length, the introducer adapted for insertion within the trocar, the length of the introducer being greater than the length of the trocar lumen portion; and a semi-rigid, bendable barb suture device comprising a central elongated suture thread having a proximal end and a distal end, a plurality of barbs extending from the suture thread, and a length, the barb suture device adapted for insertion within the introducer, the length of the suture thread being greater than the length of the introducer.

2. The system of claim 1 wherein the lumen portion of the trocar is substantially straight.

3. The system of claim 1 wherein the lumen portion of the trocar is curved to match the anatomical shape of the female patient.

4. The system of claim 1 wherein the distal end of the trocar is sharpened.

5. The system of claim 1 wherein the distal end of the introducer is curved.

6. The system of claim 5 wherein the proximal end of the introducer comprises indicia to indicate the direction of curvature of the distal end of the introducer.

7. The system of claim 1 wherein at least some of the barbs extend in the direction of the proximal end of the suture thread.

8. The system of claim 1 wherein at least some of the barbs extend in the direction of the distal end of the suture thread.

9. The system of claim 1 wherein at least some of the barbs extend in the direction of the proximal end of the suture thread and at least some of the barbs extend in the direction of the distal end of the suture thread.

10. A method for treating incontinence in a female patient comprising the steps of:

insertion of a substantially rigid trocar laterally to the female patient's urethra, the trocar comprising a lumen portion having a proximal end with a proximal opening into said lumen, a terminal end with a terminal opening into said lumen, and a handle extending laterally form the proximal end of the lumen portion;

advancement of the lumen portion of the trocar substantially parallel to the female patient's urethra until the distal end of the trocar's lumen portion reaches the top of the female patient's pubic bone;

loading of a semi-rigid, bendable barb suture device into a flexible and resilient introducer, the barb suture device comprising a central elongated suture thread having a proximal end and a distal end, and a plurality of barbs extending from the suture thread, the introducer comprising a substantially elongated hollow cylindrical body having a proximal end with a proximal opening, and a distal end with a distal opening;

insertion of the introducer loaded with the suture barb device into the trocar;

advancement of the introducer loaded with the suture barb device through the lumen portion of the trocar until the distal end of the introducer reaches the distal opening of the lumen portion;

securing the distal end of the barbed suture-type device to the female patient's tissue; and removal of the introducer and trocar while the barbed suture-type device remains in place in the tissue of the female patient.

11. The method of claim 10 wherein at least some of the barbs extend in the direction of the proximal end of the suture thread.

12. The method of claim 10 wherein at least some of the barbs extend in the direction of the distal end of the suture thread.

13. The method of claim 10 wherein at least some of the barbs extend in the direction of the proximal end of the suture thread and at least some of the barbs extend in the direction of the distal end of the suture thread.

* * * * *